Figure 1D:
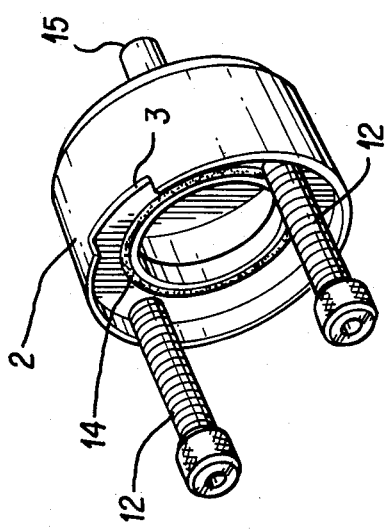
Figure 1C:
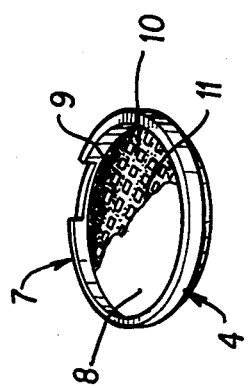
Figure 1B:
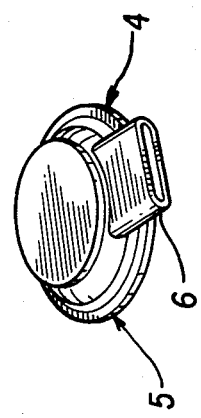
Figure 1A:
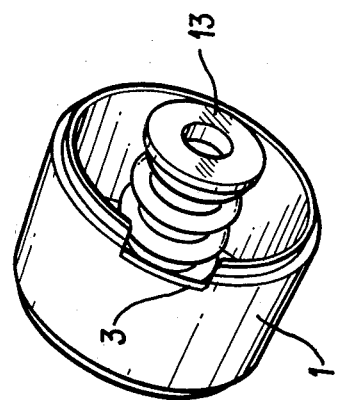

United States Patent [19]

Gibson et al.

[11] Patent Number: 4,616,513
[45] Date of Patent: Oct. 14, 1986

[54] DUST COLLECTION

[75] Inventors: Harold Gibson; Gordon Lynch, both of Edinburgh; David Mark, Stow; James H. Vincent, Haddington, all of Scotland

[73] Assignee: Coal Industry (Patents) Limited, London, England

[21] Appl. No.: 725,500

[22] Filed: Apr. 22, 1985

[30] Foreign Application Priority Data

May 3, 1984 [GB] United Kingdom ............... 8411325

[51] Int. Cl.⁴ ............................................. G01N 1/24
[52] U.S. Cl. ............................................... 73/863.23
[58] Field of Search ........... 73/863.23, 863.24, 863.25, 73/28, 863.45, 863.56, 864.32; 55/270, 400

[56] References Cited

U.S. PATENT DOCUMENTS 2,645,941 7/1953 Reid ................................. 73/863.23

FOREIGN PATENT DOCUMENTS 756380 9/1956 United Kingdom .
1228318 4/1971 United Kingdom .
1309699 4/1973 United Kingdom .
1589145 5/1981 United Kingdom .

Primary Examiner—Jerry W. Myracle
Attorney, Agent, or Firm—Stevens, Davis, Miller & Mosher

[57] ABSTRACT

A sampler for "total dust", exhibiting inspirability characteristics similar to the human head, has a filter unit containing a filter. The capsule has a lipped entry which protrudes through an aperture in a sampling head. The sampling head is connectd to suction elements for drawing an atmosphere through the filter unit and is capable of being continuously rotated.

7 Claims, 6 Drawing Figures

DUST COLLECTION

This invention concerns improvements in dust collection, more particularly it concerns a sampler especially suitable for airborne dust in workplaces.

The sampling of airborne dust for environmental health purposes has evolved in a great variety of ways. One method is to try to design a sampler which in calm or moving air has an aspiration efficiency of unity over all the particle aerodynamic diameters found; this can be considered as "true total dust". Means already exist for achieving this in calm air (for particles with aerodynamic diameters up to about 30 μm) and in moving air of well-defined speed and direction. Another approach is sought by the argument that such conditions are rarely met with in practice, and hence some research has aimed at finding a sampler which collects true total dust over a sufficiently wide range of particle sizes, wind speeds and wind orientations. No satisfactory sampler has yet been devised. A yet further approach is to consider the sampling characteristics of the human nose and mouth during breathing. Since the human body does not act as a perfect sampler but demonstrates differing aspiration efficiency with aerodynamic particle size (although relatively independent of wind speed), a total dust sampler which exhibits substantially identical collection characteristics to the inspirability curve published by Vincent and Armbruster, Ann. occup. Hyg. 24:245-248 (1981), over a range of wind speeds and orientations, would seem to be a particularly useful device for assessing dust hazards to humans.

The present invention provides a total dust sampler which closely approximates in collection characteristics to the Vincent and Armbruster curve, and which comprises a sampling head having a body with an aperture, a removable filter unit having a lipped entry which protrudes through said aperture and which unit has a filter capable of collecting all the particles in a gas passed therethrough and has a gas exit sealably engaging a gas suction means, the sampling head being drivably engaged with drive means for providing a continuous rotational movement of the sampling head. The speed of the rotational movement is not critical providing a relatively large number of rotations are achieved in the total sampling time, and may be suitably 1 to 60 rpm.

The sampler of the invention is suitable for static location in a desired location such as a workplace, and while it is especially suitable for use in underground coal mines, there are very many potential applications for sampling dust in a working environment such as the nuclear or lead industries, as the sole sampling system or additional to personal samplers. Although the embodiment particularly described hereinafter is not intended to be used in an ambient outdoors atmospheric environment, other embodiments may be engineered to provide a higher flow rate through the sampler and to contend with the problems of precipitation, insects etc.

Preferably, the sampler comprises a body enclosing the gas suction means and drive means, with the rotatable sampling head mounted on top thereof. A preferred sampling head is cylindrial, with a small elongate aperture positioned horizontally towards the middle of the external surface of the cylinder. The removable filter unit is conveniently mounted in the head, and kept in engagement, for example by biasing means, with a seal on an exit pipe which is a friction fit on a sampling pipe connected to the suction means by a suitable seal and which has a circumferential gear arrangement driven at a slow constant rate by a motor.

The removable filter unit is conveniently a sealable unit so that all the dust which enters is trapped and is eventually weighed. If only the filter were to be weighed, the dust which adheres to the inner walls of the unit would be neglected and also there would be a risk of accidental alteration of the dust collected. The filter itself is not critical provided it is able to collect all the dust particles in the particular sampling application; suitable filters are commercially available.

A preferred suction means is a diaphragm pump, suitably driven by an electric motor, powered by a battery which also provides power for the drive means.

The invention will now be described with reference to the accompanying drawings, in which FIG. 1 is an exploded perspective view of a sampling head, including filter, for one embodiment of the present invention.

Figure 2:
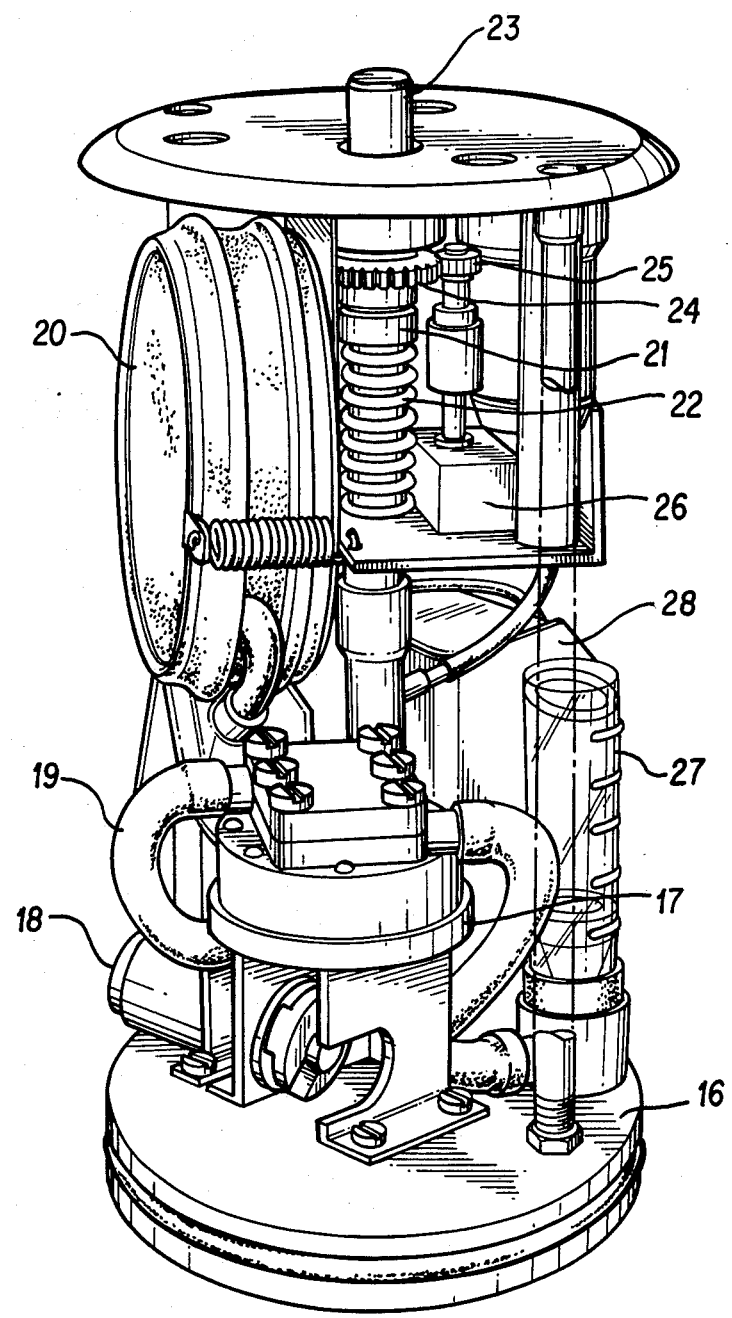
Figure 3:
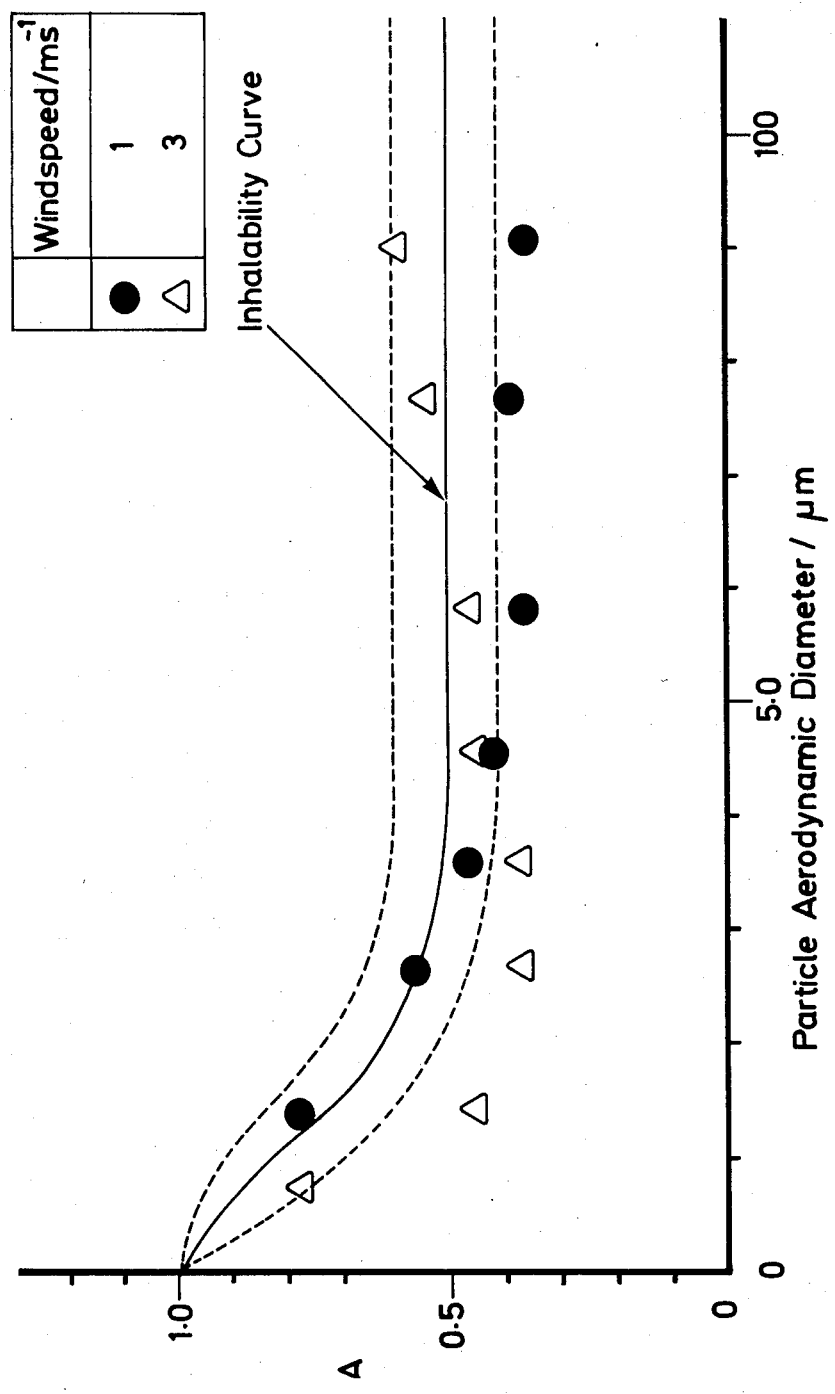

FIG. 2 is a diagrammatic view of said one embodiment without the head of FIG. 1, and FIG. 3 is a plot of results obtained in tests of the sampler of FIGS. 1 and 2, compared to the Vincent and Armbruster curve.

Referring to FIG. 1, the sampling head has a two part shell, 1, 2, each having a part slot, 3. A filter unit, 4, consists of an upper part, 5, which has a lipped elongate entry, 6, to provide access for gas flow. The lower part, 7, of the filter unit carries a filter paper, 8, seating on an annular seal, 9, and supported on a stainless steel grid, 10, and has an exit port, 11. The upper and lower parts of the filter unit are friction fitted together, the upper part engaging the filter paper in the bottom port. Shell part 1 has two holes (not shown) for bolts, 12, which are used to disassemble the head and to remove the filter unit. A spring-loaded cap, 13, mounted in shell part 1 acts to press the bottom face of the filter unit onto a synthetic rubber O-ring, 14, thus giving a sealed connection between the inside of the filter unit and an exit pipe, 15, from the head. In the assembled condition, the lipped entry 6 protrudes slightly from the external surface of the head shell.

The dimensions of the head do appear to contribute to its efficiency in modelling the inhalation characteristics of the human nose and mouth, and hence are given for the embodiment shown in the drawings. The head diameter is 50 mm and the length of the cylindrical part is 52 mm. The entry slot is 3 mm wide and 15 mm long, and the lips of the entry protrude 2 mm from the head shell. It is expected, however, that other combinations of dimensions may be found by experiment which equal or exceed the performance of this embodiment. Nevertheless, this embodiment is a convenient as well as an efficient size.

The remainder of the sampler is shown in FIG. 2, and has a base 16, on which is mounted a single acting diaphragm pump, 17, driven by an electric motor, 18. The intake side of the pump is connected by a flexible plastics tube, 19, to a flow-smoothing plenum chamber, 20. The plenum chamber in turn is connected to a PTFE tube, 21, which is biaised by a spring, 22, against the tapered end of a rotatable intake tube, 23. The intake tube 23 has an external gear, 24, driven by cog, 25, on the drive shaft of an electric motor, 26. The motor 26 provides 1.5 rpm constant rotation of the sampling head when the exit pipe 15 from the head is friction fitted into intake tube 23. The pump 17 provides a flow rate through the filter of 3 1/min, and action of the pump is monitored by a gas flowmeter, 27, connected to the output side of the pump and is controlled by means of a voltage regulator (not shown). Power for the pump and rotation motor is provided by a battery pack, 28.

The filter unit containing a fresh filter paper is weighed, fitted into the sampling head, which in turn is fitted into the intake tube and positioned in a suitable place. For example the sampler may be suspended at about head height in a work place. The pump and rotational motors are switched on and the operation of the pump is checked by looking at the flowmeter. After the desired time, conveniently a working shift, the sampler is switched off, and at some suitable time and place, the sampling head is disassembled, the filter unit removed and reweighed as a whole. Preferably, the filter unit is allowed to stabilize overnight before initial weighing and before reweighing, in a controlled environment such as a balance room.

FIG. 3 shows the results for aspiration efficiency, A, as a function of particle aerodynamic diameter obtained using the sampler at 1 m/sec and 3 m/sec wind speed, compared to the Vincent and Armbruster curve with broken lines representing the spread in results considered by Vincent and Armbruster which were associated with wind speed variation. The results from the sampler show good reproducibility and also closely resemble results obtained using human head models.

For use in underground coal mines, exposed parts at least of the sampler are made of suitable metal such as steel or brass, and attention is paid to the intrinsic safety of the electrical systems used.

We claim:

1. A total dust sampler comprising a sampling head having a protruding lipped gas entry connecting with a filter mounted within the head, a gas exit connecting with the filter and sealably engaging gas suction means, and drive means drivably engaging the sampling head which drive means is capable of providing a continuous rotational movement of the sampling head.

2. A sampler as claimed in claim 1, wherein the filter is replaceably mounted within a filter unit removable from the sampling head and which filter unit comprises the lipped gas entry and gas exit.

3. A sampler as claimed in claim 2, wherein the sampling head has an aperture and the lipped entry of the filter unit protrudes through said aperture.

4. A sampler as claimed in claim 1, wherein the sampling head is rotatably mounted on top of a body, which body contains the gas suction means and the drive means.

5. A sampler as claimed in claim 1, comprising a sampling head having an aperture and a gas unit, a filter unit having a lipped gas entry which protrudes through said aperture and which unit has a gas exit sealably engaging the gas exit of the sampling head, the sampling head being mounted above a body which body contains a gas suction pump connected to a rotatable pipe, the body also containing drive means adapted to rotatably drive the pipe, and the sampling head sealably engaging the rotable pipe.

6. A method of assessing total dust in a gas, comprising drawing the gas through the lipped entry and filter of a sampler as claimed in claim 1, while continuously rotating the sampling head.

7. A method as claimed in claim 6, wherein a filter unit containing the filter is preweighed, the filter unit is mounted within the sampling head and the sampling head is continuously rotated for a sampling time and the gas is drawn through the filter, and the filter unit is re-weighed at the end of the sampling time.

* * * * *